United States Patent
Illum et al.

(10) Patent No.: US 6,207,197 B1
(45) Date of Patent: Mar. 27, 2001

(54) GASTRORETENTIVE CONTROLLED RELEASE MICROSPHERES FOR IMPROVED DRUG DELIVERY

(75) Inventors: Lisbeth Illum, Nottingham (GB); He Ping, Miami, FL (US)

(73) Assignee: West Pharmaceutical Services Drug Delivery & Clinical Research Centre Limited, Nottingham (GB)

(*) Notice: Subject to any disclaimer, the term of this patent is extended or adjusted under 35 U.S.C. 154(b) by 0 days.

(21) Appl. No.: 09/424,145

(22) PCT Filed: May 22, 1998

(86) PCT No.: PCT/GB98/01513

§ 371 Date: Nov. 18, 1999

§ 102(e) Date: Nov. 18, 1999

(87) PCT Pub. No.: WO98/52547

PCT Pub. Date: Nov. 26, 1998

(30) Foreign Application Priority Data

May 24, 1997 (GB) .................................................. 9710699

(51) Int. Cl.⁷ .............................. A61K 9/16; A61K 9/50
(52) U.S. Cl. ........................ 424/491; 424/493; 424/495
(58) Field of Search .................................. 424/455, 489, 424/493, 501, 462, 491, 497, 495

(56) References Cited

U.S. PATENT DOCUMENTS

| 4,772,475 | * | 9/1988 | Fukui et al. ............... 424/468 |
|---|---|---|---|
| 4,844,905 | | 7/1989 | Ichikawa et al. . |
| 4,895,724 | | 1/1990 | Cardinal et al. . |
| 5,198,229 | | 3/1993 | Wong et al. . |
| 5,338,731 | * | 8/1994 | Breuer et al. ............... 514/108 |
| 5,571,533 | | 11/1996 | Santus et al. . |
| 5,603,961 | * | 2/1997 | Suzuki et al. ............... 424/502 |
| 5,736,161 | * | 4/1998 | Garces et al. ............... 424/493 |
| 5,955,096 | * | 9/1999 | Santos et al. ............... 424/434 |
| 5,972,389 | * | 10/1999 | Shell et al. ............... 424/501 |

FOREIGN PATENT DOCUMENTS

| 0 392 487 | 10/1990 | (EP) . |
|---|---|---|
| 0 486 959 | 5/1992 | (EP) . |
| 0 516 141 | 12/1992 | (EP) . |
| 0 635 261 | 1/1995 | (EP) . |
| 63-020302 | 1/1988 | (JP) . |
| 5-339149 | 12/1993 | (JP) . |
| WO 85/02092 | 5/1985 | (WO) . |
| WO 92/18143 | 10/1992 | (WO) . |
| WO 93/15737 | 8/1993 | (WO) . |
| WO 93/21906 | 11/1993 | (WO) . |
| WO 94/00112 | 1/1994 | (WO) . |

OTHER PUBLICATIONS

Atyabi, et al., "In vivo evaluation of a novel gastric retentive formulation based on ion exchange resins," *J. Control. Rel.* 42:105–13 (1996).

Babu & Khar "In vitro and in vivo studies of sustained–release floating dosage forms containing salbutamol sulfate," *Pharmazie.* 45(4):268–70 (1990).

Burton, et al., "Intragastric distribution of ion–exchange resins: a drug delivery system for the topical treatment of the gastric mucosa," *J. Pharm. Pharmacol.* 47(11):901–06 (1995).

(List continued on next page.)

Primary Examiner—Thurman K. Page
Assistant Examiner—Liliana Di Nola-Baron
(74) Attorney, Agent, or Firm—Arnall Golden & Gregory, LLP

(57) ABSTRACT

There is provided a drug delivery composition for the controlled release of an active agent in the stomach environment over a prolonged period of time, which comprises a microsphere comprising an active ingredient in the inner core of the microsphere and (i) a rate controlling layer of a water insoluble polymer and (ii) an outer layer of a bioadhesive agent in the form of a cationic polymer.

22 Claims, 5 Drawing Sheets

OTHER PUBLICATIONS

Bechgaard & Ladefoged, "Distribution of pellets in the gastrointestinal tract. The influence on transit time exerted by the density or diameter of pellets," *J. Pharm. Pharmacol.* 30(11):690–92 (1978).

Cargill, et al., "Controlled gastric emptying. 1. Effects of physical properties on gastric residence times of nondisintegrating geometric shapes in beagle dogs," *Pharm. Res.* 5(8):533–36 (1988).

Clarke, et al., *Gastrointestinal Transit of Spherical Granules of Differing Size and Density*, PhD Thesis, University of London, 1989.

Ch'ng, et al., "Bioadhesive polymers as platforms for oral controlled drug delivery II: synthesis and evaluation of some swelling, water–insoluble bioadhesive polymers," *J. Pharm. Sci.* 74(4):399–405 (1985).

Deshpande, et al., "Controlled–release drug delivery systems for prolonged gastric residence: an overview," *Drug Devel. Ind. Pharm.* 22:531–39 (1996).

Fiebrig, et al., "Sedimentation analysis of potential interactions between mucins and a putative bioadhesive polymer," *Progress in Colloid Polymers Sci.* 94:66–73 (1994).

Gurny & Junginger, *Bioadhesion Possibilities and Future Trends*, Wissenschafliche Verlaggeschelchaft, 1990.

Inouye, et al., "Buoyant sustained release granules based on chitosan," *Drug. Des. Deliv.* 4(1):55–67 (1989).

Longer, et al., "Bioadhesive polymers as platforms for oral controlled drug delivery III: oral delivery of chlorothiazide using a bioadhesive polymer," *J. Pharm. Sci.* 74(4):406–11 (1985).

Martindale, *The Extra Pharmacopoeia*, 31$^{st}$ edition, Royal Pharmaceutical Society (1996).

Mazer, et al., "Intragastic behavior and absorption kinetics of a normal and "floating" modified–release capsule of isradipine under fasted and fed conditions," *J. Pharm. Sci.* 77(8):647–57 (1988).

Miyazaki, et al., "Substained–release and intragastric–floating granules of indomethacin using chitosan in rabbits," *Chem. Pharm. Bull.* 36(10):4033–38 (1988).

Moes, "Gastroretentive dosage forms," *Crit. Rev. Ther. Drug Carrier Syst.* 10(2):143–95 (1993).

Ohya, et al., "Release behaviour of 5–fluorouracil from chitosan–gel microspheres immobilizing 5–fluorouracil derivative coated with polysaccharides and their cell specific recognition," *J. Microencapsul.* 10(1):1–9 (1993).

Park & Park, "Enzyme–digestible balloon hydrogels for long–term oral drug delivery: synthesis and characterization," *Proc. Int. Symp. Control. Rel. Bioact. Mater.* 14:41–42 (1987).

Polk, et al., "Controlled release of albumin from chitosan–alginate microcapsules," *J. Pharm. Sci.* 83(2):178–85 (1994).

Rathbone & Heatley, "Possible pathogenic mechanisms in *Helicobacter pylori* infection," *Campylobacter pylori and Gastroduodenal Disease* p. 217–23, Blackwell:London, 1989.

Wozniak, *Analytical Profiles of Drug Substance*, 19, (K. Florenz, Ed.), p. 397–427, Academic Press: San Diego, (1990).

Yao, et al., "Microcapsules/Microspheres related to chitosan," *J.M.S.—Rev. Macromol. Chem. Phy.* C35:155–80 (1995).

Drug Facts and Comparisons. 1997 Edition. Pp. 634–645. Facts and Comparisons. St.louis. A Wolters Kluwer Company.*

* cited by examiner

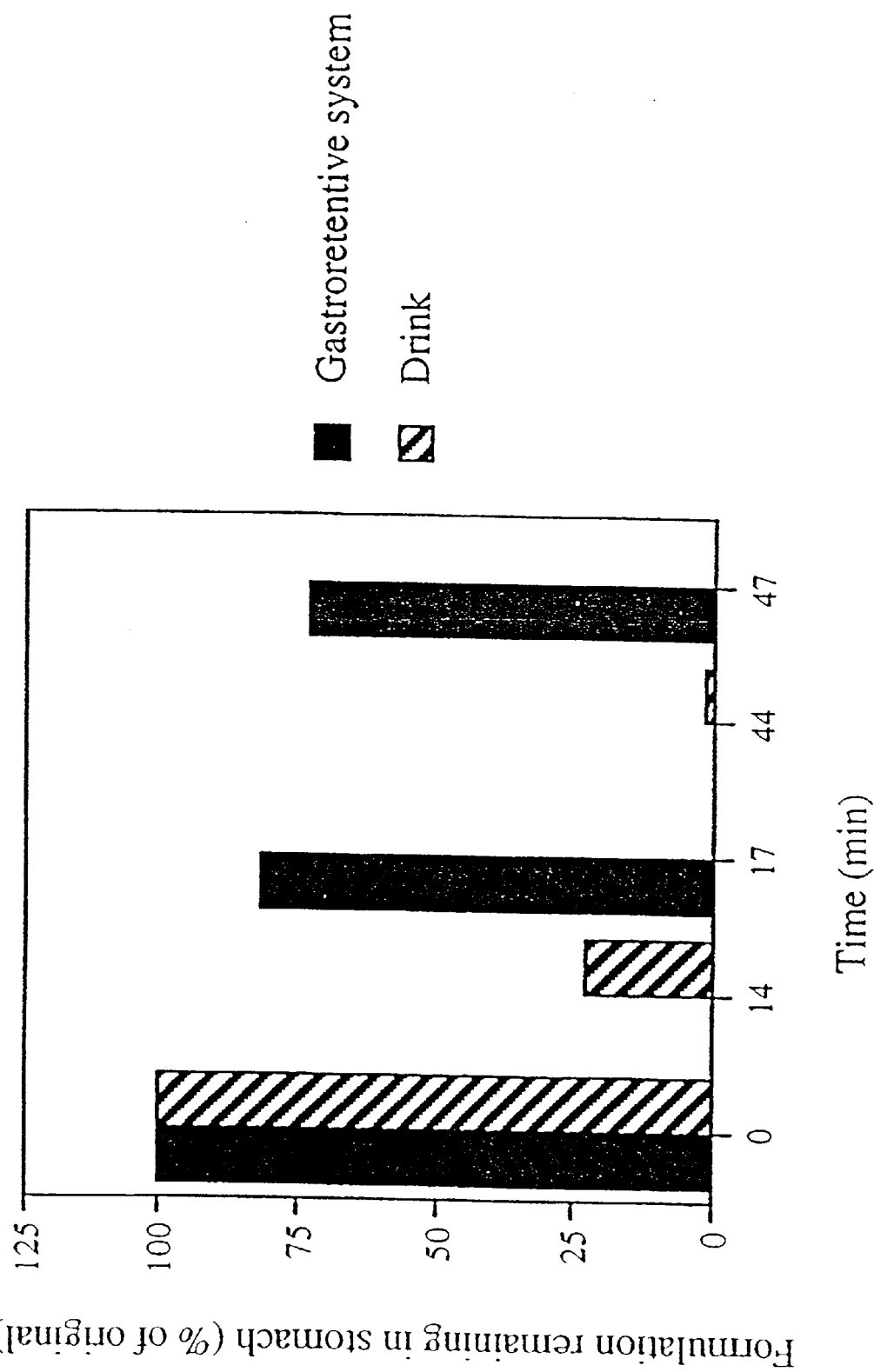

GASTRORETENTIVE CONTROLLED RELEASE MICROSPHERES FOR IMPROVED DRUG DELIVERY

Priority is claimed under 35 U.S.C. § 119 to PCT/GB98/01513, filed May 22, 1998, which corresponds to GB 9710699.1 filed May 24, 1997.

FIELD OF THE INVENTION

This invention relates to a novel method for retaining pharmaceutical agents in the stomach of a mammal, in order to provide local treatment of diseases of the stomach, or to improve the intestinal absorption of drugs which have a limited absorption capacity in the small intestine of such a mammal.

BACKGROUND

The preferred route for the administration of most drugs is via the gastrointestinal tract Most drugs are well absorbed from throughout the entire intestinal tract, but some compounds, usually those which are polar in nature, are poorly absorbed from the large intestine. For such drugs, the main area from which absorption occurs is the small intestine. Some drugs may exploit a natural pathway, such as receptor-mediated transport, active transport or other specific transport mechanisms, and are known to have socalled "absorption windows" in the small intestine. The term "absorption windows" describes the fact that a drug will be absorbed from a limited region of the intestine rather than the whole of the small and large intestines. The "window" could represent the duodenum, the jejunum or the ileum or parts thereof. Examples of such drugs include methyldopa and captopril. It would be advantageous to hold these drugs, which may display less than ideal absorption behaviour from the small intestine, in the stomach above their main absorption site for extended time periods, for example by way of a gastroretentive drug formulation.

A gastroretentive system would also be of value in the administration of a drug which is intended to produce a local effect in the stomach. A good example of this type of therapy is provided by way of the w ell known use of antibiotics in the local treatment of *Helicobacter pylori* (*H. pylori*) Furthermore, the use of antimicrobial substances for the treatment of *Camplobacter pylori* (with the additional treatment with other substances sach as $H_2$-receptor blockers) is suggested in an article by Hirsche and Pletschelte (1989) (*Campylobacter pylori* and *Gastroduodenal Ulcers* Rathbone and Heatley, eds.), Blackwell (1989) p. 217). More particularly, these authors also suggest that, if retention in the stomach could be achieved, drugs which demonstrate topical activity could be readily administered orally for local treatment.

Various methods have been proposed in the prior art to achieve gastroretention, including dosage forms which display extended residence in the stomach due to their density or size, or through the use of mechanisms based on a putative bioadhesion concept.

The topic of gastroretentive dosage forms has been well reviewed by Moes (*Crit. Rev. Ther. Drug Carrier Syst.*, 10, 143 (1993)) and Deshpande el al (*Drug Devel. Ind. Pharm.*, 22, 531 (1996)). Proposed methods described in these review articles for prolonging the gastric residence time of drug delivery systems include agents such as fatty acids, pharmacological agents which delay the passage of material from the stomach to the small intestine, and devices such as unfolding polymer sheets and balloon hydrogels (Park, K. and Park, H., Proc. *Int. Symp. Control. Rel. Bioact. Mater.*, 14, 41 (1987) and Cargill R., Caldwell, I. J., Engle, K., Fix, J. A., Porter, P. A., and Gardner, C. R., *Pharm. Res.*, 5, 533, 1988). While the concept of using large single unit dosage forms for gastric retention is attractive at first sight, potential problems, including blockage of the oesophagus or small itesine in certain patient groups, are known to be associated.

A further way to retain a drug delivery system in the stomach for an extended time period is to administer a nondisintegrating tablet or capsule, of a size greater than about 7 mm, and less than 20 mm, together with a large meal. The nature processes of gastric motility ensure that a delivery system of this size does not normally exit from the stomach until the stomach is empty of food. Thereafter the delivery system is cleared into the intestine through the action of a physiological process known as the migrating myoelectric complex (Phase III activity). However, in many instances, where drug absorption is affected by food, it would be advantageous to dose therapeutic agents to an empty, fasted stomach.

In the case of local treatment of gastric disorders, it would also be beneficial to achieve close adherence of a drug delivery system to the mucosal surface of the stomach, once the stomach has been emptied of liquid/food. Previous attempts to achieve this effect have not been successful, and no beneficial increase in residence time in man has been reported. By "beneficial increase in residence time" in this context, we mean that the residence time in the stomach for patients in the fasted state is at least three times greater than that for a control solution formulation.

The use of bioadhesive polymers as gastroretentive materials has been well reviewed in the pharmaceutical literature and is the subject of patent applications (see, for example, Ch'ng, H. S., Park, H., Kelly, P., and Robinson, J. R., *J. Pharm. Sci.*, 74, 399 (1985); Longer, M. A., Ch'ng, H. S., and Robinson, J. R., *J. Pharm. Sci.*, 74, 406 (1985); and Gurney and Junginger (Eds.) *Bioadhesion Possibilities and Future Trends*, Wissenschafliche Verlaggeschelchaft (1990)).

Tablets and pellets with increased gastric retention and bioadhesive properties have been described in international patent application WO 94/00112. The specific use of microadherent formulations in the treatment of gastric disorders (including *H. pylori*) has been described in international patent application WO 92/18143. Natural gums, plant extracts, sucralfate, acrylic acid or methacrylic acid derivatives are suggested as means to give sustained release and/or prolonged retention in the stomach.

Controlled release mucoadhesive microgranules for the oral administration is of furosemide are described in U.S. Pat. No. 5,571,533. The granules are made from lipophilic excipients and are coated with mucoadhesive anionic polymers selected from the group: carbomer, polycarbophil, hydrodroxypropyl methyl cellulose, hydroxypropyl cellulose or admixtures thereof.

Moes (1993) (see reference above) reports that the use of bioadhesive polymers to modify gastrointestinal transit has been abandoned since such mucoadhesive polymers are not able to control or slow down significantly the gastrointestinal transit of solid delivery systems, such as pellets and tablets Pellets and other single units with a high density have also been investigated for gastroretention in Bechgaard, H. and Ladefoged, K., *J. Pharm. Pharmacol.*, 30, 690 (1978) and Clarke, G. M. *Gastrointestinal Transit of Spherical Granules of Differing Size and Density*, PhD Thesis (1989), University of London), but the approach has not led to significant advantage in man unless the specific gravity is greater than 2.0. The skilled person will appreciate that such a high density presents a considerable disadvantage in a conventional pharmaceutical product from the standpoint of processing and weight.

Low density (floating systems) in the form of pellets and tablets have also been reported (Babu et al, *Pharmazie*, 45, 268 (1990); Mazer et al, *J. Pharm. Sci.* 77, 647 (1988)). Whilst some small benefits can be demonstrated, such systems in their own right do not appear to provide extended periods of residence in the stomach. However, they do offer some protection against early and random gastric emptying, though, in order to do this, need to be administered immediately after a meal Floating minicapsules, having a size 0.1 to 2 mm, containing sodium bicarbonate, and which are coated by conventional water soluble film coating agents are described in U.S. Pat. No. 4,106,120. Similar floating granules based on gas generation have been described in U.S. Pat. No. 4,844,905. Floating capsules have also been described in U.S. Pat. No. 5,198,229. Atyabi et al, (*J. Control. Rel.*, 42, 105 (1996)) have described ion exchange systems containing bicarbonate that release $CO_2$ on contact with hydrochloric acid in the stomach, which gas is then trapped within a semi-permeable membrane surrounding the beads. This causes the particles to float. A suitable coating agent is disclosed as being Eudragit RS. The particles may then be given with food, though testing the formulation in question under the rigorous conditions of a fasted stomach is not described in the document in question. Moreover, no drug was incorporated into the particles to provide a slow release.

Burton et al (*J. Pharm. Pharmac.*, 47, 901 (1995)) studied gastroretention of an ion-exchange resin in the form of negatively charged fine particles in comparison with an aqueous solution in man. They found that the first 60 to 70% of the resin cleared at the same rate as an aqueous phase but the remaining 30 to 40% of the resin was retained for an extended period. All subjects were dosed after an overnight Neither drug loaded microspheres nor gastroretentive systems with controlled release properties are mentioned or suggested.

European patent application EP 635 261 describes coated microparticles with improved drug absorption which consist of dehydrated microparticles comprising a nucleus of a gellable hydrocolloid onto which is deposited a film of cationic polysaccharide. The microparticles described in this document promote the absorption of drugs from the intestine. Gastroretention is not mentioned (on the contrary, it is suggested that the microparticles may be contained in an enterically coated gelatin capsule to protect the particles until they enter the duodenum). Incorporated within the matrix of the microparticles of EP 635 261 is a pharmacologically-useful drug. The hydrocolloids are preferably agar, pectin, xanthan gum, guar gum, locust bean gum, hyaluronic acid, casein and water soluble salts of alginic acid. The procedure for obtaining the microspheres is characterised by a multi-step process in which a solution of the gellable hydrocolloid is added to a medium in which gelling of the hydrocolloid takes place (eg calcium chloride). The microparticles so formed are separated and suspended in a concentrated solution of the drug from which the drug diffuises into the microparticles The microparticles are then separated and suspended in a solution of cationic polysaccharide (such as diethylaminodextran) to effect deposition of the polysaccharide onto the surface of the spheres. After this, the covered spheres are separated, washed and dried. No indication is given as to how the drug is retained in the particle during these various processing stages. The use of a rate controlling membrane as part of the composition of the microparticle is not mentioned. Moreover, no mention is made of the preparation of microparticles by spray drying.

Chitosan microspheres and microcapsules have been described previously as drug carrier systems. A review has been published by Yao et al (J.M.S.—i Rev. Macromol. Chem. Phy., C35, 155 (1995)). In order to make such systems, chitosan is cross-linked with an agent such as glutaraldehyde. Chitosan microcapsules, produced via a complex coacervation process, are also known. Alginate is a suitable negatively charged agent which may interact with positively charged chitosan (see for example, Polk et al, *J. Pharm. Sci.* 83, 178 (1994)). Sustained release and floating granules based on chitosan have been described by Miyazaki et al, *Chem. Pharm. Bull.*, 36, 4033 (1988) and Inouye et al, *Drug Des. Deliv.*, 4, 55, 1989. However, the particles mentioned in these documents are large in size and do not contain a release rate modifying polymer.

Chitosan compositions for controlled and prolonged release of macromolecules have been described in U.S. Pat. No. 4,895,724. A porous matrix of chitosan is described, in which the macromolecule is dispersed It is stated that the chitosan may be crosslinked by various agents to include glutaraldehyde, glyoxal, epiclorohydrin and succinaldehyde The use of microspheres for bioadhesion or gastroretention is not suggested.

Chitosan microspheres have been described by others, for use in oral delivery, (Ohya et al, *J. Microencaps.*, 10, 1 (1993); JP 5339149, EP 486 959, EP 392 487). However, such particles have not been prepared with a view to providing a controlled release effect.

In a recent international patent application (WO 93/21906) a range of bioadhesive polymers in the form of, or as coatings on, microcapsules containing drugs. is described. Chitosan is described as performing poorly in bioadhesive tests. Moreover, the method of preparation of the chitosan microparticles may have rendered them negatively charged.

Thus, in summary, it would be of benefit to provide a system for delivering drug to the stomach which possessed the following attributes:
- a significant retention time in the fasted stomach of mammalian (e.g. human) subjects
- a high loading of water soluble and lipid soluble drugs
- a controlled release of such drugs over a period of time that is relevant to the clinical need (ie delivery of drug to the stomach, and/or enhanced drug uptake from an absorption window in the small intestine).

Other desirable attributes include:
- the preparation of such a formulation using established pharmaceutical processing methods
- the use of materials in the preparation of such a formulation that are approved for use in foods or pharmaceuticals or of like regulatory status.

DESCRIPTION OF THE INVENTION

We have found, surprisingly, that microspheres comprising an inner core (optionally including a gelled hydrocolloid) containing a therapeutic agent (ie active ingredient or drug), a rate controlling membrane of water insoluble polymer (such as ethylcellulose) and an outer layer of a bioadhesive cationic polymer, which polymer may comprise a cationic polysaccharide, a cationic protein and/or a synthetic cationic polymer, may provide the necessary performance criteria, indicated above.

According to a first aspect of the invention, there is provided a drug delivery composition for the controlled release of an active ingredient in the stomach environment over a prolonged period of time which comprises a microsphere, which microsphere comprises an active ingredient in its inner core, and (i) a rate controlling layer of a water insoluble polymer and (ii) an outer layer of a bioadhesive agent in the form of a cationic polymer (hereinafter referred to as "the compositions of the invention").

Typically, the compositions of the invention are in the form of a plurality of microspheres that, upon administration to a mammal along with a suitable fluid (e.g. water), float initially on the stomach contents, and have a surface that provides a beneficial interaction between the particles and the mucus lining of the stomach, or with the wall of the stomach itself, when the stomach is emptied of liquid/food. The microsphere inner cores, which contain the drug in a sustained release system, are coated with a cationic polymer. The rate controlling layer can be either part of the inner core of the microsphere containing drug or present as a separate layer. Drug may be dispersed uniformly (homogeneously) or non-uniformly (heterogeneously) throughout the inner core. The compositions of the invention may provide release of drug in the stomach environment (ie the gastric area) of the gastrointestinal tract over a prolonged period of time (e.g. at least twice as long as the stomach takes to empty itself of water (under normal conditions)).

For the purpose of this invention, by "microspheres", we include microparticles, which are substantially spherical and of "microns size and microcapsules (which are microspheres or microparticles where the drug is encapsulated rather than dispersed homogeneously in the matrix). By "Substantially spherical" we mean microparticles with a good sphericity (e.g. more than 80% of the particles have a longest measurable diameter which is less than or equal to two times greater in length than the shortest measurable diameter, as determined by light microscopy).

The microspheres may have a size in the range 0.5 to 1000 µm, more preferably in the range 1 to 700 µm and most preferably 5 to 500 µm, (mean volume diameter (MVD)) as measured using a laser diffraction method. We have found that the above size ranges give good retention in the stomach. Larger particles such as pellets and granules of a size greater than 1000 µm (eg 1000 to 2000 µm) do not adhere well.

We have found that the compositions of the invention have a low density and initially float on the contents of the stomach following administration with a suitable dosing liquid. When the stomach is emptied of its contents, the particles adhere to, and coat, the stomach wall.

Cationic polymers which may be used as bioadhesive agents in the outer layer include synthetic cationic polymers and, particularly, cationic polysaccharides and cationic proteins. The material is chosen such that the microspheres carry a net positive charge, greater than +0.5 mV, more preferably greater than +5.0 mV, and most preferably greater than +10 mV (as measured by the technique of micro electrophoresis) at pH 4 in 0.001M buffer (such as a phosphate buffer, McIlvanes buffer, HEPES buffer).

Chitosan in the form of a salt is a preferred choice for use as the cationic bioadhesive material. Chitosan is non-toxic and is present in the diet. It is a positively charged biopolymer at gastric pH. It is known that chitosan may interact with negatively charged sialic acid groups in mucin (Fiebrig et al, *Progress in Colloid and Polymers Sci.*, 94, 66 (1994)).

Chitosan is prepared by the deacetylation of chitin. The degree of deacetylation of chitosan should be greater than 40%, preferably greater than 60% and most preferably greater than 80%. The chitosan should have a molecular weight of greater than 5,000 D, preferably greater than 10,000 D and most preferably greater than 50,000 D. Chitosan can be employed as a chitosan salt (eg the glutamate, lactate, chloride or acetate salt) or as a chitosan derivative such as N-trimethyl chitosan chloride.

Other suitable bioadhesive cationic polymers which may be used include acidic (high isoelectric point) gelatin, polygalactosamine, proteins (polyaminoacids) such as polylysine, polyornithine, polyquaternary compounds, prolamine, polyimine, diethylaminoethyldextran (DEAE), DEAE-imine, polyvinylpyridine, polythiodiethylaminomethylethylene (PTDAE), polyhistidine, DEAE-methacrylate, DEAE-acrylamide, poly-p-aminostyrene, polyoxethane, copolymethacrylates (eg copolymers of HPMA, N-(2-hydroxypropyl)-methacrylamide), Eudragit® RL, Eudragit® RS, GAFQUAT (see U.S. Pat. No. 3,910, 862), polyamidoamines, cationic starches, DEAE-dextra and DEAE-cellulose. The polycationic substances used in the invention have a molecular weight of more than 5,000 D, preferably at least 50,000 D.

Preferred water insoluble polymers for use in the a rate controlling layer include ethylcellulose and polymethylmethacrylate. By "water insoluble polymer", we mean a polymer with a solubility in distilled water at pH 7 of less than 1 mg/mL at room temperature. The rate controlling layer and the cationic polymer may or may not comprise the same material (e.g. polymethylmethacrylate).

When the drug employed in the composition according to the invention is a polar drug, the inner core of the microsphere may further comprise a gelled hydrocolloid (i.e. a hydrocolloid that gels during microsphere production to provide structure (a reticulating agent)) with the therapeutic agent. Suitable hydrocolloid substances which may be employed include gelatin, albumin and alginates, for example agar, pectin, xanthan gum, guar gum, locust bean gum, hyaluronic acid, casein and water soluble salts of alginic acid. Gelling hydrocolloids may be gelled via appropriate means known to those skilled in the art (e.g. cooling of aqueous solutions, interaction with metal ions etc.)

By "polar drug" we mean a compound with a partition coefficient between water and octanol at pH 7.4 of less than 500.

The compositions of the invention may be provided by way of processes that produce compositions which provide for entrapment of the drug and its slow release in the stomach (see above) Thus, the compositions of the invention may be prepared via a variety of techniques, such as emulsification followed by solvent evaporation under vacuum, spray coating etc. However, we have also found that the compositions of the invention may be prepared conveniently by way of an emulsification process combined with spray drying.

For polar drugs (which includes water soluble drugs), a novel double mulsion procedure (water-in-oil-in water; w/o/w) may be used. We have found, surprisingly, that this particular method may be used to prepare floating microspheres that are positively charged and have controlled release properties, and is especially suitable for water soluble drugs.

Oil is defined herein as any liquid with a solubility in water of less than 2 mL (oil) in 10 mL (water) (i.e. it is immiscible with water)

By "water soluble" drugs, we include drugs which have sufficient solubility (eg more than 1 mg/mL, preferably more than 10 mg/mL) in the internal water phase of a double (w/o/w) emulsion, to enable the formation of microspheres from a subsequent spray drying process having a drug loading which is sufficiently high (eg more than 10%) to permit administration of the compositions of the invention so produced in a conventional capsule formulation or similar oral dosing system, such as a cachet or sachet, the content of which may be administered for example by, for example, dispersing in water and drinking.

In the preparation of compositions of the invention comprising polar drugs via an emulsification process, the water insoluble polymer which is used in the rate controlling layer may be dissolved in the oil phase.

For non-polar drugs, an oil-in-water (o/w) emulsification process may be used. In each case, the emulsions may be subsequently spray dried. By "non-polar drugs" we include drugs which are sufficiently soluble (i.e. more than 1 mg/mL, preferably more than 10 mg/mL) in an organic solvent (which solvents include dichloromethane, chloroform, ethyl acetate etc.), such that it drug is able to dissolve in the selected organic phase of an oil-in-water emulsion system in a sufficient quantity to enable the formation of microspheres from a subsequent spray drying process having a drug loading which is sufficiently high (eg greater than 10%) to permit administration of the compositions of the invention so produced in a conventional single unit hard capsule (eg one made from gelatin or starch) or a similar oral dosing system such as a cachet or sachet which content is administered by, for example, dispersing in water and drinking.

In the preparation of compositions of the invention comprising non-polar drugs, the therapeutic agent can be dissolved in the same solvent (ie the oil phase) that is used for the rate controlling layer.

It will be appreciated by the skilled person that the drug may be dissolved in the internal phase of the emulsion which is used, or can be suspended therein (depending on its solubility in his phase).

In the case of both polar and non-polar drugs, the bioadhesive cationic polymer is provided in an aqueous phase, being either the aqueous phase of the oil-in-water emulsion, or the external aqueous phase of the water-in-oil-in-water emulsion. Emulsions systems may be prepared in accordance with techniques which are well known to those skilled in the art, such as those described hereinafter.

When the compositions of the invention are produced by way of the emulsion processes described above, appropriate concentrations for use in the compositions of the invention are that the gelling hydrocolloid (if used) concentration for the preparation of the internal phase of the double emulsion is from 0.1% to 30%, preferably from 0.5 to 20%. The rate controlling layer is provided at a concentration of 0.5% to 20% in a suitable organic solvent, preferably from 1% to 10%. The organic solvent is preferably dichloromethane. The bioadhesive cationic polymer concentration used for the preparation of the external phase of the double emulsion is from 0.05 to 10% w/w but preferably from 0.1 to 5% and most preferably from 0.2 to 2%. Drug concentration may be from 0.01 to 90% depending on the drug which is employed. The above percentages are expressed as the weight of the particular component in the appropriate phase of the emulsion in which it is provided.

Following the formation of an appropriate emulsion system, the compositions of the invention may conveniently be prepared by spray drying, under conditions which are well known to those skilled in art. For example, the preparation of simple chitosan microspheres by spray drying chitosan dissolved in dilute acetic acid has been described in the prior art by Sugaya (Jpn. Kokai Tokyo Koho, JP 6320302). We have found that spray drying is a process for the preparation of microparticles for use with pharmaceuticals which can be scaled up readily.

The emulsion formulation can then be formed into microspheres using a suitable spray drying apparatus. Suitable apparatus include that described hereinafter in the examples Other suitable equipment which may be employed include the apparatus available from Buchi in Switzerland, Niro/Aeromatic-Fielder (Switzerland/USA), LabPlant (UK) and Yamamoto (Japan). The operating conditions such as the flow rate of the solution into the spray dryer, the size of the nozzle, the inlet and outlet air temperature, the atomization pressure, and the flow rate of the drying air, can be adjusted in accordance with the appropriate manufacturer's guidelines in order to provide the required particle size and release properties for the resultant microspheres. Such operation conditions can be easily selected by the person skilled in the art of pharmaceutical formulation paying proper attention to known methods of experimental design.

According to a further aspect of the invention there is provided a process for the preparation of a composition of the invention which comprises the spray drying of an oil-in-water, or a water-in-oil-in-water, emulsion including the components of the composition.

An improved gastric retention can be achieved for the compositions of the invention by increasing the pH of the stomach above the normal fasting range (1.5 to 2.5). Thus, the sialic acid residues in the mucus will be largely in the ionised form and will interact strongly with the cationic polymer. Certain foods can also produce an increase in pH to above pH 5 that lasts for a period of 30 minutes or longer. Patients receiving $H_2$-antagonists, proton pump inhibitors or antacids represent a special case, in which an advantage is provided by virtue of the fact that the gastric pH will be raised to 4 by the effect of the drug. Raising pH in this way may be particularly useful in the treatment of *H. pylori* infection.

Thus, according to a further aspect of the invention, there is provided a kit of parts for use in the treatment of *H. pylori* infection, including a composition comprising an $H_2$-antagonist, a proton pump inhibitor or an antacid and a composition of the invention including a drug suitable for the treatment of *H. pylori*.

The compositions of the invention may, where appropriate, be surface hardened by, for example, and where appropriate, partially cross-linking by glutataidehyde, formaldehyde, benzydianone, benzoqimone, tolyphosphate or other cross-linking agents known to persons skilled in the art, in order to provide an intact bioadhesive surface layer that does not dissolve rapidly in the stomach and thereby fail to provide a beneficial bioadhesive effect. The conditions for carrying out the cross-linking, such as the amount of cross-linking agent required, are determined by monitoring the zeta potential of the microparticles and adjusting the process conditions until the required zeta potential (as determined for example by the technique of particle microelectrophoresis in a buffer of low ionic strength (0.001M) at a pH of 4.0) is obtained. The compositions of the invention carry a net positive charge, which is believed to provide a beneficial effect by allowing interaction with the negatively charged sialic acid groups of mucin.

The compositions of the invention may be administered to a mammal in suitable dosage forms, in accordance with techniques, and via delivery devices, all of which are known to those skilled in the art, for example by way of a capsule, a powder or as a compressed tablet, administered by mouth, that dissolves in the stomach to release the bioadhesive particle. The compositions may be administered with a suitable dosing liquid (e.g. water).

Active ingredients which may be included in the compositions of the invention include those which are suitable for the local treatment of disorders of the stomach as well as compounds that typically display limited absorption from the gastrointestinal tract due to a limited absorption from the small intestine. Active ingredients which are usefull in the treatment of diseases affecting the stomach include those suitable for the treatment of *H. pylori* infection, as well as $H_2$-antagonists and proton pump inhibitors. The following list is intended to provide examples and is not intended to be exclusive: metronidazole, ampicillin, doxycycline, tetracycline, oxytetracycline, itraconazole, ranitidine, cimetidine, famotidine, nizatidine and omeprazole.

Drugs that display preferential absorption from the small intestines and may be used in the compositions of the invention can be found in all therapeutic categories. A nonexclusive list is as follows: levodopa, methyldopa, fuirosemide, carvedilol, atenolol, topiramate, hydrochlorothiazide, captopril and orlistat (and other drugs for the treatment of obesity).

Combinations of the abovementioned therapeutic agents/active ingredients may also be employed.

For the avoidance of doubt, the term "therapeutic agents" is intended herein to include agents which are suitable for use in the treatment, and in the prevention, of disease.

The compositions of the invention may be used to treat/prevent diseases/conditions in mammalian patients depending upon the therapeutic agent(s) which is/are employed. For the above, nonl-exhaustive, lists of drugs, diseases/conditions which may be mentioned include those against which the therapeutic agent(s) in question are known to be effective, and include those specifically listed for the drugs in question in Martindale, "*The Extra Pharmacopoeia*", 31st Edition, Royal Pharmaceutical Society (1996).

The amount of therapeutic agent which may be employed in the compositions of the invention will depend upon the agent which is used, and the disease to be treated, but may be in the range 0.1 mg to 10 g. However, it will be clear to the skilled person that suitable doses of therapeutic agents can be readily determined non-inventively. For example, estimates of dosage can be made from known injectable products assuming that from 0.1 to 100% of the dose is absorbed. Suitable single unit doses may be in the range 100 μg to 1000 mg depending upon the therapeutic agent(s) which is/are employed and the route of administration. Suitable daily doses are in the range 100 μg to 5 g/day depending upon the therapeutic agent(s) which is/are employed.

The compositions of the invention may be dosed once, or more (eg three) times, daily depending on the condition to be treated.

The compositions may also contain other additives in the form of pharmaceutical excipients, such as preservatives (e.g. low concentrations of materials such as sodium metabisulphate), stabilisers, flavouring agents, absorption enhancers such as bulking agents (e.g. lactose, microcrystalline cellulose), glidants and lubricants, bile salts, phospholipids and enzymatic inhibitors.

Compositions of the invention have the advantage that they may possess a significant retention in the fasted stomach of mammalian (e.g. human) subjects, may be used to incorporate a high loading of water soluble and lipid soluble drugs and may provide a controlled release of such drugs over a period of time that is relevant to the clinical need.

Furthermore, compositions of the invention have the advantage that they may be used to assist in the retention of pharmaceutical agents in the stomach of a mammal, in order to provide local treatment of diseases of the stomach, or to improve the intestinal absorption of drugs which have a limited absorption capacity in the small intestine of such a mammal, depending on the drug which is used.

Moreover, compositions of the invention also have the advantage that they may be prepared using established pharmaceutical processing methods and employ materials in that are approved for use in foods or pharmaceuticals or of like regulatory status.

According to a further aspect of the invention there is provided a method of treatment or prophylaxis of a disease which comprises administration of a composition of the invention including a therapeutic agent which is effective against said disease to a patient in need of such treatment.

The invention is illustrated, but in no way limited, by the following examples, in which Examples 1 to 4 aim to demonstrate that, when employing certain methods, some of which are described in the prior art, it is not possible to produce a microsphere with a suitable performance. The subsequent Examples (5 to 7) are illustrative of the instant invention where controlled release gastroretentive microspheres can be prepared using a novel emulsion-spray drying method (water in oil in water (w/o/w) and oil in water (o/w) emulsions). Example 8 demonstrates that compositions of the invention display enhanced retention in the stomach of human subjects.

The examples refer to the figures, in which:

FIG. 5 shows a histogram illustrating gastric emptying of a formulation comprising disodium clondromate tetrahydrate loaded microspheres prepared by a w/o/w emulsion-spray drying method.

EXAMPLE 1

Preparation of Non-Crosslinked Chitosan Microspheres

Figure 1:
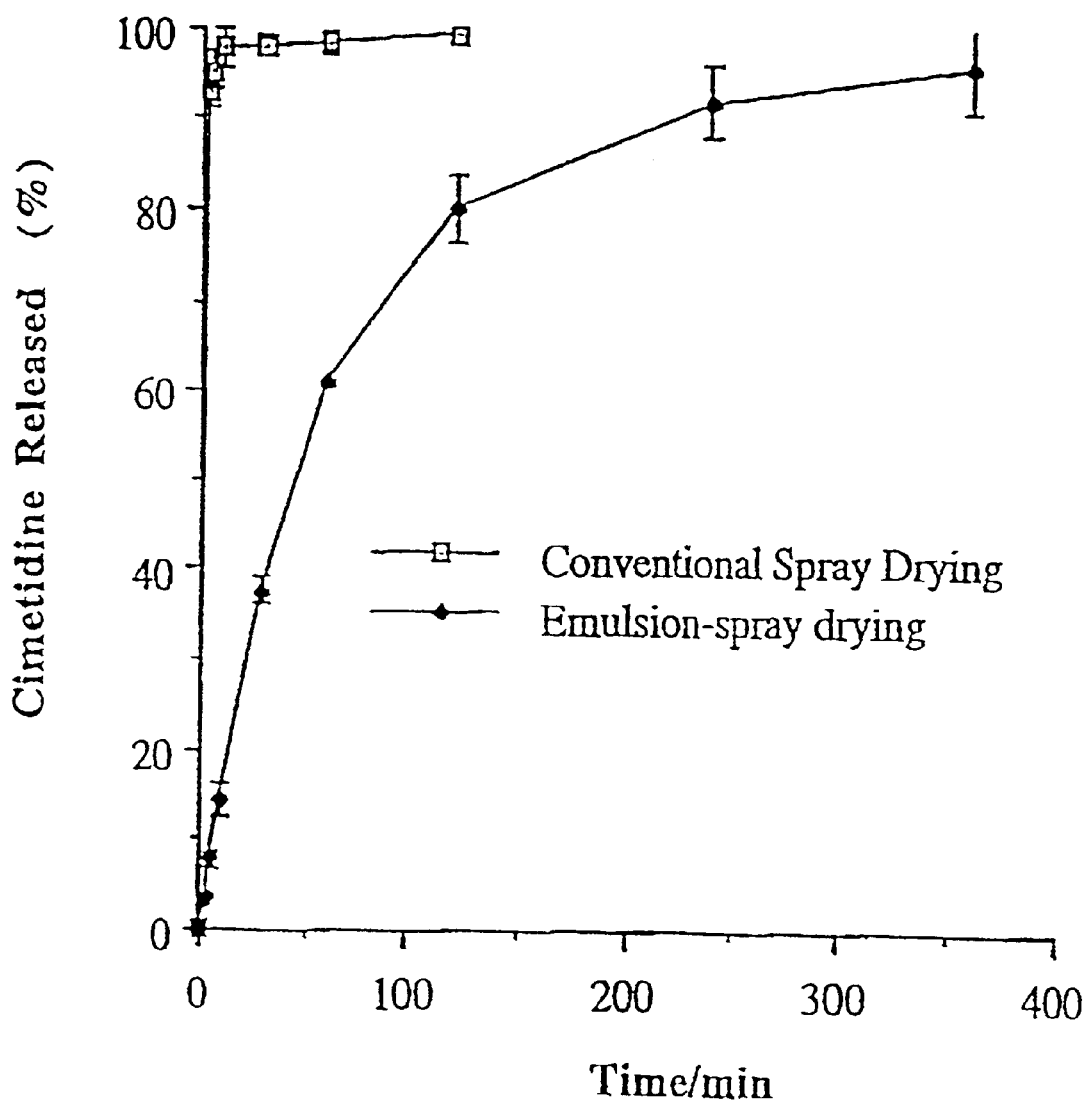
FIG. 1 shows the release profile of cimetidine loaded microparticles prepared by w/o emulsion-spray drying method.

Chitosan hydrochloride salt (0.3 to 0.4 g; Seacure CL 210 obtained from Pronova, Norway) was weighed into a 50 mL beaker and 20 mL of water was added to dissolve the chitosan. The resulting solution was made up to a volume of 100 mL using water and used for the spray drying process. Co-current spray drying was performed using a SD-04 spray drier (Lab Plant, England), with a standard 0.5 mm nozzle. The inlet temperature was controlled at 160° C. The spray flow rate was controlled at 6 mL/min. The compressed spray air flow (represented as the volume of the air input) was set at 10 L/min. The resultant particles had good sphericity as determined by light microscopy (Nikon Optiphot) 20 or 40X magnification and were of a mean size of 6 micron (mean volume diameter (MVD)) as measured using a laser diffraction method (Malvern Mastersizer Model MS 1002). The particles carried a positive zeta potential (surface charge) of +27 mV as determined in 0.001M acetate buffer at pH 4.0 using a Malvern Zetasizer mark IV. For this measurement 1 to 3 mg of microspheres were dispersed in the buffer system.

However, the microspheres prepared by this method were found to swell in water, dissolve quite rapidly in pH 2.0 buffer (the conditions of the stomach). Such microspheres would therefore have a short lifetime in the stomach and have no controlled release characteristics, and thus be unsuitable for controlled drug delivery and gastroretention.

EXAMPLE 2

Preparation of Crosslinked Chitosan Microspheres, with No Rate-Controlling Layer, Using Spray Drying In order to produce stable chitosan microspheres that would not swell and dissolve, drug free microspheres were prepared by a spray drying process using formaldehyde and glutaraldehyde as cross-linking agents.

The process used was as described in Example 1, but prior to spray drying, a defined amount of an aqueous solution of formaldehyde or glutaraldehyde was added to the chitosan solution The chitosan concentration was 0.1%. The defined amounts of cross-linking agent were 0.5, 1.0, 2.0, 4.0, 8.0 mL of a 1% formaldehyde solution and 0.5, 1.0, 1.5, 2.0, 4.0, 8.0 and 16.0 mL of a 1% glutaraldehyde solution.

The microspheres so produced had good sphericity. The size of those produced using cross-linking using formaldehyde were in the range 1.75 to 3.2 $\mu$m (MVD), the zeta potential, as measured in 0.001M pH 4 acetate buffer ranged from +16 to +20 mV. The greater the quantity of cross-linking agent, the lower the positive zeta potential. Similarly for glutaraldehyde cross-linked systems, the size (MVD) ranged from 1.5 to 3.7 $\mu$m and the zeta potential from +21 to +14.5 mV; as previously, the greater the quantity of cross-linking agent, the lower the positive potential. When 0.2% chitosan solution was used with the same quantities of glutaraldehyde, the particles still had good sphericity but were somewhat larger in size (range from 8.8 to 2.3 $\mu$m; MVD). The zeta potentials were similar to those obtained with 0.1% chitosan solution. These microspheres did not contain drug; similar microspheres are prepared below which include drugs.

EXAMPLE 3

Preparation of Drug Loaded Microspheres Using Spray Drying

Microspheres were prepared using a method similar to that in Example 2.

10 mg of cimetidine was added to 500 mL of 0.1% or 250 mL of 0.2% chitosan aqueous solution A specific amount of 2% glutaraldehyde aqueous solution or 1% formaldehyde aqueous solution was added with stirring using a magnetic stirrer. The spray drying was effected following the procedure as in Example 1.

The properties of the microspheres were as follows: The microspheres were found to be spherical in all cases. Drug loading was approximately 17% w/w. The size ranged from 2.0 to 7.9 $\mu$m (MVD) depending on the initial concentration of the chitosan used (0.1% or 0.2%) and the amount of cross-linking agent added (1 to 4 mL of 4% glutaraldehyde). The zeta potentials at pH 4.0 in 0.001M acetate buffer were in the narrow range of +15 to +17 mV. Similar results were obtained using formaldehyde as the cross-linking agent.

Drug loading was measured as follows: a defined amount of drug-loaded chitosan microspheres, accurately weighed, was placed in a 50 mL volumetric flask. The mixture was dispersed and diluted to volume with 0.1N sulphuric acid. The suspension was sonicated in an ultrasonic bath (Decon FS 100) for 10 minutes and held overnight at room temperature to allow the drug to filly dissolve from the microspheres. 5 mL of the suspension was filtered with a 0.2 $\mu$m syringe filter to remove particulate material and the absorbance was determined. The drug contents were measured spectrophotometrically.

In vitro release was determined as follows: an in vitro test was carried out using a dissolution apparatus (Copley-Erweka DT-6) with the dissolution paddle assembly (USP Apparatus 2 or BP Apparatus 11). Samples were suspended in 300 mL of pH 7.4 phosphate buffered saline at 37° C., at 50 rpm agitation rate. A specific amount of drug loaded microspheres. accurately weighed, was added into each vessel. 3 mL of the sample was drawn into a syringe at predetermined time internals. The same amount of the fresh dissolution medium was added to the system. The samples were filtered and the drug content measured spectrophotometrically. Pure unincorporated free drug was used as a control. The dissolution measurements showed that the release of the $H_2$-antagonist from the chitosan microspheres prepared by the spray drying method was extremely rapid. The majority of the drug was released in less than 15 minutes and the dissolution profile was essentially similar to the unincorporated drug.

Thus, while cross-linked chitosan microspheres of a small particle size and positive charge and with good drug loading could be prepared, the release of the incorporated drug was very rapid and tile products prepared would be of no clinical value.

EXAMPLE 4

Preparation of Controlled Release Microspheres Using a Water-in-Oil Emulsification Process Followed by Spray Drying The work described in the examples above clearly demonstrate that simple stabilised chitosan microspheres as described in the prior art are not suitable as gastroretentive systems that provide controlled release of an incorporated drug. In order to delay drug release, an alternative process was investigated using an emulsification process where ethylcellulose was employed as a drug retention agent. In addition the water soluble drug was first dissolved in gelatin so as to provide a reticulation agent to provide a physical structure to the inside of the spray dried microspheres so produced.

0.1 g of gelatin A and 0.1 g of drug (cimetidine or famotidine) were weighed into a 16 mL test tube. 5 mL of distilled water was added. A clear solution was obtained when the mixture was heated to 60° C.

0.4 g of the water insoluble polymer ethylcellulose (EC-Dow) was dissolved in 50 mL of dichloromethane in a 100 mL beaker. The aqueous solution containing the drug and gelatin was added dropwise it the oil phase under magnetic string. This system was then homogenized at 11,000 rpm for 2 minutes. The water-in-oil (w/o) emulsion formed was directly spray dried under the following conditions: Co-current spray drying was performed using a SD-04 spray drier (Lab Plant, England) with a standard 0.5 mm nozzle. The inlet temperature was controlled at 50° C. The spray flow rate was controlled at 8 mL/min.

TABLE 1

Characteristics of microparticles prepared by a w/o emulsion-spray drying method

| Drug | Drug content (%) | Size ($\mu$m) | Zeta potential (mV:pH 7)* |
|---|---|---|---|
| Cimetidine | 15.5 | 6.04 | −4.0 |
| Famotidine | 12.8 | 10.09 | −3.3 |

*Phosphate buffer 0.0001M

The physico-chemical characteristics of the particles prepared by w/o emulsion-spray drying method are shown in Table 1. Poor sphericity was observed The particle size was about 10 $\mu$m. Since a positively charged material, eg. chitosan, was not used in this example, the particles so prepared were negatively charged.

Drug release from the microparticles prepared by the w/o emulsion-spray drying method was carried out in a dissolution apparatus as previously described. The release profile of the cimetidine loaded microparticles prepared by w/o emulsion-spray drying method is shown in FIG. 1. Cimetidine release from the particles was greatly retarded, compared with the drug loaded microspheres prepared by the conventional spray drying method with chitosan, as described in Example 1. The drug was released gradually over several hours.

The microparticles were seen to float on the surface of the dissolution medium. The addition of a wetting agent to the dissolution medium in the form of 0.05% Tween 80 gave rise to an increased release rate.

EXAMPLE 5

Preparation of Controlled Release Microspheres by an Oil-in-Water (o/w) Emulsion/Spray Drying Method In those situations where the drug is sufficiently soluble in the organic solvent it is possible to prepare a drug loaded microsphere using an oil in water emulsion. Here the oil phase which contains the drug and ethylcellulose (or other suitable controlled release polymers) is dispersed in the aqueous chitosan solution and then spray dried. This method can be exemplified using the $H_2$-antagonist nizatidine.

0.1 g nizatidine and 0.2 g ethylcellulose were dissolved in 5 mL of dichloromethane in a 16 mL test tube. It was added dropwise into 100 mL 0.4% chitosan aqueous solution under magnetic stirring Homogenization was performed at 12,500 rpm for 1 minute and the mixture sonicated if necessary. After the addition of 2 mL of 4% glutaraldehyde aqueous solution, the emulsion was spray dried. Cocurrent spray drying was performed using a SD-04 spray drier (Lab Plant, England) with a standard 0.5 mm nozzle. The inlet temperature was controlled at 13° C. The spray flow rate was controlled at 6 mL/min. The air flow rate was set at 10 L/min. The sphericity for the drug loaded microparticles was good. The particle size of the drug loaded microspheres was 7.7 $\mu$m (MYD). The zeta potential at pH 4.0 at an ionic strength of 0.001M was +9.0 mV. The drug loading was 8.4% w/w.

Figure 2:
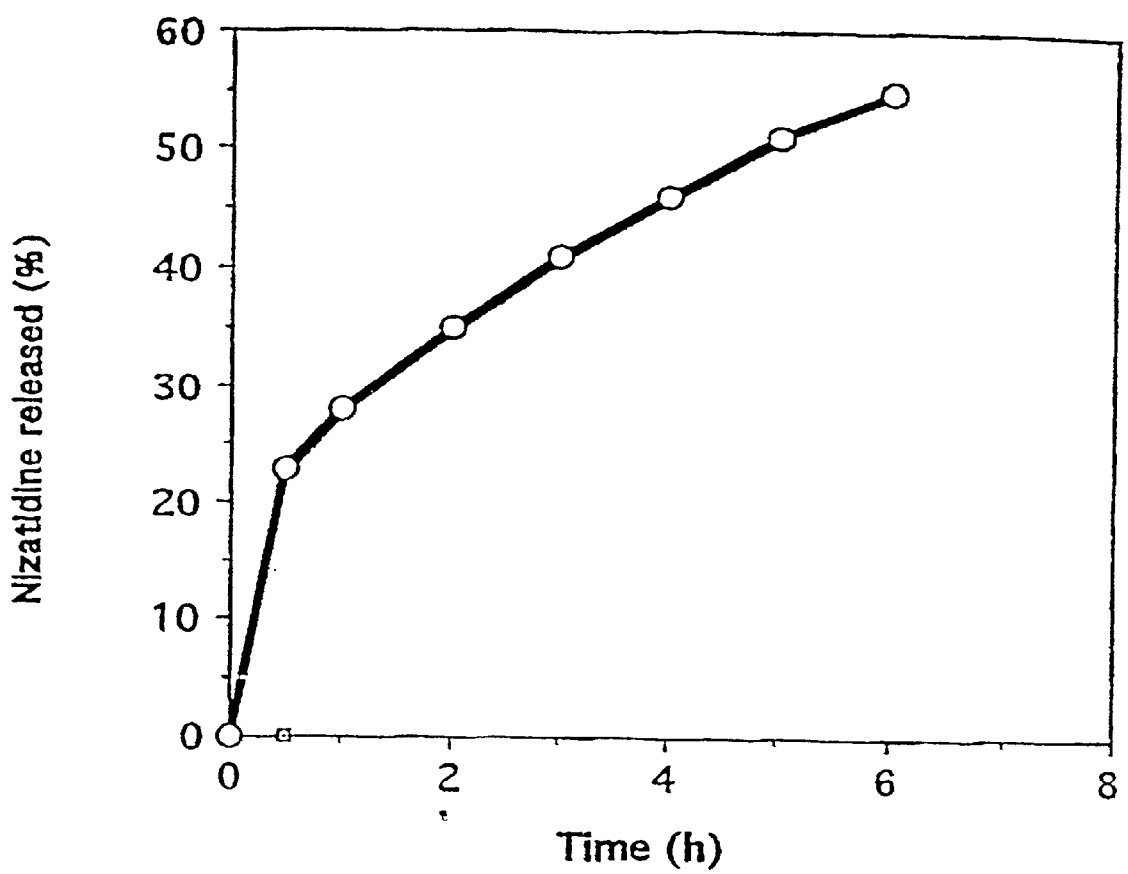
FIG. 2 shows the release profile of nizatidine loaded microparticles prepared by o/w emulsionspray drying method.
Figure 3:
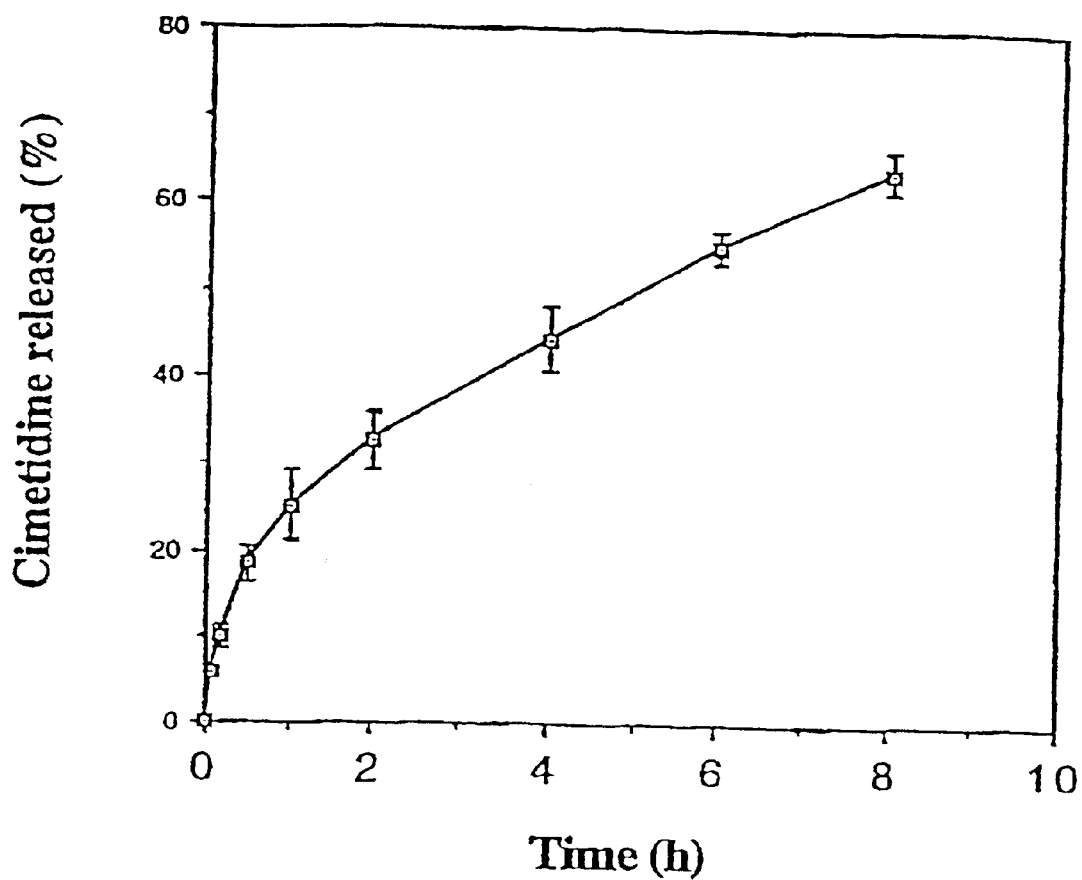
FIG. 3 shows the release profile of cimetidine loaded microparticles prepared by w/o/w emulsion-spray drying method.
Figure 4:
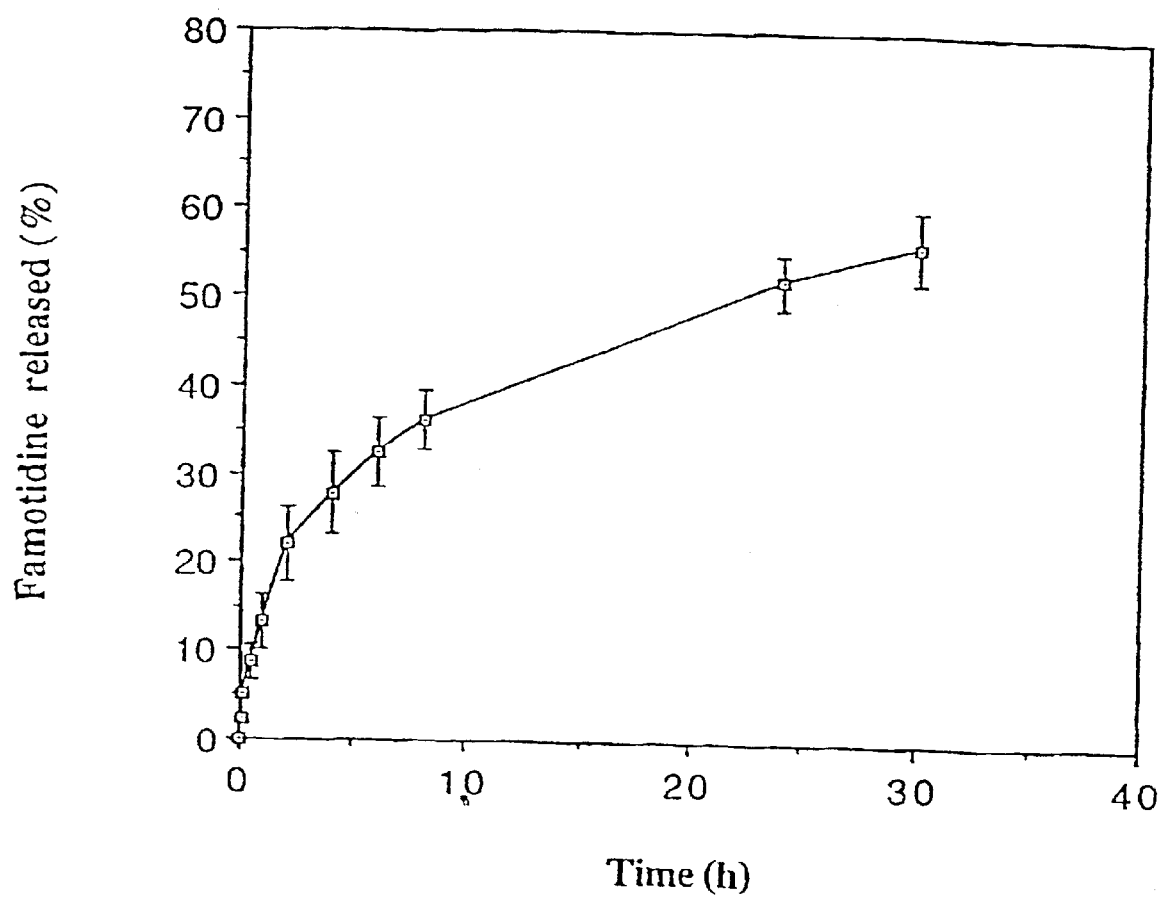
FIG. 4 shows the release profile of famotidine loaded microparticles prepared by w/o/w emulsion-spray drying method.

The release of drug was measured using the USP dissolution method as described in Example 3. The concentration of nizatidine was measured by an ultraviolet spectroscopic method at 313 nm according to the method of Wozniak (*Analytical Profiles of Drug Substances*, 19, Ed. K. Florenz, Academic Press, San Diego, p. 397, 1990). A controlled release profile was obtained (FIG. 2).

EXAMPLE 6

Preparation of Floating Microspheres Prepared by a Novel w/o/w Emulsion Spray Drying Method Chitosan microspheres prepared by a conventional-spray drying method as described in Example 3 had a good sphericity and were positively charged. However, the rate of release of $H_2$-antagonist from the microspheres was fast and accompanied by a "burst effect". Drug release from the microparticles prepared by a w/o emulsion-spray drying method as described in Example 4 was retarded, but the particles are not gastroretentive. In the following method, positively charged microspheres were prepared.

0.1 g of gelatin type A and 0.1 g of a water soluble drug (cimetidine or famotidine) were weighed into a 16 mL test tube. 5 mL of distilled water was added. A water phase consisting of a clear solution was obtained when the mixture was heated to 60° C. This is termed the internal phase. An oil phase consisted of 0.2 gram of ethyl cellulose (Dow), dissolved in 25 mL of dichloromethane in a 50 mL beaker. An external water phase was composed of 150 mL of 0.3% chitosan (MW 140–160 kD) aqueous solution in a 200 mL beaker.

The internal water phase was added dropwise into the oil phase under magnetic stirring. The system was then homogenized using a Silverson homogenizer (Silverson, Chesham, Bucks, UK) at 11,000 rpm for 2 minutes. Sonication was performed if necessary. This primary emulsion was then added dropwise into the external water phase under magnetic stirring. Further homogenizing was provided at 10,000 rpm for 2 minutes. 2 mL of 4% glutaraldehyde was used as a cross-linking agent before spray drying. Co-current spray drying was performed using a SD-04 spray drier (Lab Plant, England), with a standard 0.5 mm nozzle. The inlet temperature was controlled at 150° C. The spray flow rate was controlled at 6 mL/min. Drug free microspheres were prepared according to the same procedure, without addition of the drug.

The characteristics of the drug free microspheres prepared by w/o/w emulsion-spray drying method are listed in Table 2. The formation of the w/o/w double emulsion was confirmed using light microscopy (before spray drying) and the characteristics of the floating behaviour of the formed microspheres were also evaluated using a suitable dissolution medium (USP-simulated gastric fluid). Under scanning electron microscopy, their particles were seen to be hollow when fractured, which demonstrates the low density and potential floating characteristics. The w/o/w emulsion formed was very good, as assessed by light microscopy, in that the "oil particles" were seen to contain water droplets. The size of the w/o/w emulsion droplets and harvested microspheres were dependent upon mixing rate and nozzle mounting position of the spray drying apparatus. A last rate of mixing (or sonication) led to a smaller particle size. Larger microspheres were produced by counter-current spray drying. The emulsion particles formed were about 20–40 $\mu$m in diameter.

After the solvent of the emulsion was removed by evaporation, the size of the particles was reduced to about 10 to 15 μm. In order to prepare microspheres with a size of 10 μm, and with a floating character, a procedure was adopted where the mixing rate for both primary and secondary emulsion was set at 12,600 rpm for 1 minute followed by conventional concurrent spray drying.

The characteristics of the drug-loaded microspheres so prepared are shown in Table 3. The particle size was similar to that for drug free microparticles. The particles were positively charged. The drug loading was high. The sphericity was acceptable.

An in vitro test was carried out using a dissolution apparatus as described hereinbefore. The dissolution paddle assembly (USP Apparatus 2 or BP Apparatus II) was used. However, the basket assembly (USP Apparatus 1 or BP Apparatus 1) was used. The microspheres were filled into hard gelatin capsules. Samples were weighed into the capsules individually and were released into 300 to 500 mL of pH 7.4 phosphate buffered saline or simulated gastric fluid, containing different amount of the surfactant Tween 80 (used to evaluate the influence of the amount of the wetting agent on the rate of release). The temperature and agitation were set at 37° C. and 50 rpm, respectively. 3 mL of the dissolution sample was drawn into a syringe at predetermined time intervals. The same amount of the fresh dissolution medium was supplied to the system. The samples were filtered with 0.2 μm syringe filters. The contents of the drug were measured spectrophotometrically.

TABLE 2

Characteristics of the drug free microspheres prepared by the w/o/w emulsion/spray drying method

| Mixing rate for the emulsion | | Size of w/o/w Emulsion (μm) | Size of Harvested Microspheres (μm) | Floating |
|---|---|---|---|---|
| Primary | Secondary | | | Character |
| 12,600;1 min | 12,600;1 min | <20 | 9.71 | + |
| 12,600;30 sec | 12,600;30 sec | 40–80 | 16.41 | ++ |
| 12,600;1 min* | 12,600;30 sec | 5–10 | 7.71 | + |
| 12,600;1 min | 12,600;30 sec | 20–40 | 20.93** | + |

*Sonication for the primary emulsion
**Counter-current spray drying
+ good degree of floating ability
++ excellent degree of floating ability

What is claimed is:

1. A drug delivery composition for the controlled release of an active ingredient in the stomach environment over a prolonged period of time, comprising a microsphere which comprises
   an active ingredient in the inner core of the microsphere,
   a rate controlling layer of a water insoluble polymer, and
   an outer layer of a bioadhesive agent in the form of a cationic polymer.

2. The drug delivery composition of claim 1 wherein the cationic polymer is selected from the group consisting of cationic polysaccharides, cationic proteins, and synthetic cationic polymers.

3. The drug delivery composition of claim 1 wherein the inner core contains a gelling hydrocolloid.

4. The drug delivery composition of claim 1 wherein the water insoluble polymer is ethylcellulose.

5. The drug delivery composition of claim 1 wherein the cationic bioadhesive agent is chitosan.

6. The drug delivery composition of claim 1 wherein the cationic bioadhesive agent is diethylaminoethyldextran.

7. The drug delivery composition of claim 3 wherein the gelling hydrocolloid is gelatin.

8. The drug delivery composition of claim 1 made by spray drying an oil-in-water or a water-in-oil-in-water emulsion including the active ingredient, the water insoluble polymer, and the cationic polymer.

9. The drug delivery composition of claim 1 wherein the active ingredient is useful in the local treatment of a disease of the stomach.

10. The drug delivery composition of claim 1 wherein the active ingredient has a limited absorption capacity in the small intestine of a mammal.

11. The drug delivery composition of claim 1 wherein the active ingredient is useful in the treatment of *Helicobacter pylori*.

12. The drug delivery composition of claim 1 wherein the active ingredient is useful in the treatment of *Campylobacter pylori*.

13. The drug delivery composition of claim 1 wherein the active ingredient is an $H_2$-antagonist or a proton pump inhibitor.

14. The drug delivery composition of claim 1 wherein the active ingredient is a bisphosphonate.

15. The drug delivery composition of claim 1 in a pharmaceutically acceptable dosage form suitable for oral administration.

16. A method for the treatment or prophylaxis of a disease, the method comprising
   administering to a patient in need of such treatment or prophylaxis a composition comprising a microsphere which comprises
      an active ingredient effective against the disease, wherein the ingredient is in the inner core of the microsphere,
      a rate controlling layer of a water insoluble polymer, and
      an outer layer of a bioadhesive agent in the form of a cationic polymer.

17. The method of claim 16 wherein the disease is one of the stomach, and wherein the active ingredient is useful in the local treatment of the disease.

18. A kit of parts for use in the treatment of *H. pylori* infection, the kit comprising
   a composition comprising an $H_2$-antagonist, a proton pump inhibitor, or an antacid, and
   a composition comprising a microsphere which comprises
      an active ingredient useful in the treatment of *Helicobacter pylori*, wherein the ingredient is in the inner core of the microsphere,
      a rate controlling layer of a water insoluble polymer, and
      an outer layer of a bioadhesive agent in the form of a cationic polymer.

19. A process for the preparation of a composition for the controlled release of an active ingredient in the stomach environment over a prolonged period of time, the process comprising
   preparing an oil-in-water or a water-in-oil-in-water emulsion comprising the active ingredient, a water insoluble polymer and a cationic polymer, and
   spray drying the emulsion to yield microspheres having
      the active ingredient in the inner cores of the microspheres,
      a rate controlling layer of the water insoluble polymer, and
      an outer layer of a bioadhesive agent in the form of the cationic polymer.

20. A method of delivering a therapeutic agent to the stomach of a patient, the method comprising administering to the patient a composition comprising a microsphere which comprises the therapeutic agent in the inner core of the microsphere, a rate controlling layer of a water insoluble polymer, and an outer layer of a bioadhesive agent in the form of a cationic polymer.

21. A method of enhancing the gastrorentention of an active ingredient in the stomach of a patient, the method comprising administering to the patient the active ingredient in a composition comprising a microsphere which comprises the active ingredient in the inner core of the microsphere, a rate controlling layer of a water insoluble polymer, and an outer layer of a bioadhesive agent in the form of a cationic polymer.

22. A method of enhancing the gastrointestinal absorption of a drug which has a limited absorption capacity in the small intestine of a patient, the method comprising administering to the patient the drug in a composition comprising a microsphere which comprises the drug in the inner core of the microsphere, a rate controlling layer of a water insoluble polymer, and an outer layer of a bioadhesive agent in the form of a cationic polymer.

* * * * *